United States Patent [19]

Whitesides et al.

[11] Patent Number: 4,701,285
[45] Date of Patent: Oct. 20, 1987

[54] ACYL PHOSPHATE SALTS AND THEIR USE

[75] Inventors: George M. Whitesides, Newton; Debbie C. Crans; Romas J. Kazlaukas, both of Cambridge, all of Mass.

[73] Assignee: Massachusetts Institute of Technology, Cambridge, Mass.

[21] Appl. No.: 793,722

[22] Filed: Oct. 31, 1985

Related U.S. Application Data

[63] Continuation of Ser. No. 591,174, Mar. 19, 1984.

[51] Int. Cl.$^4$ ........................................... C07C 153/00
[52] U.S. Cl. .................................. 260/545 P; 435/89; 435/92; 435/140
[58] Field of Search ................ 260/545 P; 435/89, 92, 435/140

[56] References Cited

U.S. PATENT DOCUMENTS 4,088,675  5/1978  Whitesides et al. ............. 260/545 P

OTHER PUBLICATIONS

Lynen, Feodor "Uber die gemischten Anhydride aus Phosphorsaure und Essigsaure" Chem. Ber. vol. 73 (1940) pp. 367–375.
Lipmann, F. and Tuttle, L. C. "Acetyl Phosphate: Chemistry, Determination, and Synthesis" J. Biol. Chem. vol. 153 (1944) pp. 571–582.
Bentley, Ronald "A New Synthesis of Acetyl Dihydrogen Phosphate" J. Amer. Chem. Soc. vol. 70 (1948) pp. 2183–2185.
Stadtman, E. R. & Lipmann, F. "Acetyl Phosphate Synthesis by Reaction of Isopropenyl Acetate and Phosphoric Acid" J.Biol. Chem. v.185 (1950) pp. 549–551.
Koshland, D. E., Jr. "Kinetics of Peptide Bond Formation" J. Amer. Chem. Soc. vol. 73 (1951) pp. 4103–4107.
Avison, A. W. D. "The Synthesis of Acyl Phosphates in Aqueous Solution" J. Chem. Soc. vol. 732 (1955) pp. 732–738.
Porter, R. W., et al. "Aspartate Transcarbamylase-Kinetic Studies of the Catalytic Subunit" J. Biol. Chem. vol. 244 (1969) pp. 1846–1859.
Heyde, E. et al. "Mechanism of the Reaction Catalyzed by the Catalytic Subunit of Aspartate Transcarbamylase. Kinetic Studies with Carbamyl Phosphate as Substrate" Biochemistry vol. 12, No. 23 (1973) pp. 4718–4726.
Whitesides, et al. "Large-Scale Synthesis of Diammonium Acetyl Phosphate" J. Org. Chem. vol. 40 (1975) pp. 2516–2519.

Primary Examiner—Paul J. Killos
Assistant Examiner—L. Hendriksen
Attorney, Agent, or Firm—James E. Maslow; Thomas J. Engellenner

[57] ABSTRACT

This invention consists of the production of a salt of acyl phosphate in an aqueous solution by a process which involves (1) acylation of phosphoric acid ($H_3PO_4$) with an acid anhydride of the general formula RCOX, where R can be hydrogen or a lower alkyl or aryl group having from 1 to 10 carbon atoms, and X can be a leaving group of the general formula OR, OCOR, X or $NR_2$, followed by (2a) extraction of acyl phosphate to water by treatment of the reaction mixture with an aqueous bicarbonate or hydroxide solution or other basic aqueous solution, if the reaction is carried out in non-aqueous solvent or (2b) in the case where water has been used as reaction solvent acidification with acid or acid form of a carbon exchange resin. After (3) extraction of residual carboxylic acid from the resulting acidic aqueous mixture using a solvent in which the acid is soluble but with which water does not mix, the remaining aqueous solution of acyl phosphate is (4) neutralized by addition of a base such as sodium or potassium hydroxide.

13 Claims, No Drawings

ACYL PHOSPHATE SALTS AND THEIR USE

This application is a continuation of application Ser. No. 591,174, filed Mar. 19, 1984.

BACKGROUND OF THE INVENTION

The U.S. Government has rights in this invention pursuant to a grant from the National Institute of Health No. NIH-5-PO1-CA12174-12. This invention deals with the preparation of salts of acyl phosphoric acids, such as disodium acetyl phosphate. Such compounds are useful in the production of phosphorylating agents such as adenosine triphosphate (ATP), a required cofactor in many reactions in the biosynthesis of materials such as protein, carbohydrates, nucleotides, nucleic acids, and terpenes.

Biosynthesis by enzymatic catalysis has been attracting increased attention as a means of large scale production of many complex products. See, e.g., Skinner, "Enzymes Technology," Chem. & Engin. News, Vol. 53, No. 33, p. 22 (Aug. 18, 1975). A major limitation on the commercial usefulness of such processes, however, has been the cost of many of the cofactors or coenzymes necessary to conduct the reactions involved. For example, ATP is a cofactor which plays a prominent role in many biosynthetic processes, promoting formation of chemical bonds which otherwise would not form in significant quantities in dilute aqueous solutions. See generally, Stadtman, The Enzymes, Vol. 8, Chapter 1 3rd ed. 1972). For the use of ATP in cell-free enzymatic synthesis, see Baughn et al., J. Am. Chem. Soc., 100, 304 (1978), Wong et al., Methods Enzymol. 89, 108 (1982), all incorporated herein by reference. The high cost of cofactors such as ATP has severely inhibited the use of such processes on a commercial scale.

In order to reduce the cost of enzymatic synthesis requiring ATP, a system has been developed to regenerate ATP enzymatically from adenosine diphosphate (ADP) and/or adenosine monophosphate (AMP). Normally, treatment of the raw materials used in biosynthesis with ATP to form more complex products results in the consumption of ATP and the production of AMP and/or ADP. Under the regeneration system, if AMP is produced in the biosynthesis, it is converted to ADP by enzyme catalyzed phosphoryl transfer from ATP according to the following equation:

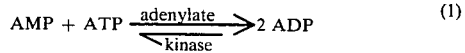  (1)

The ADP is then converted to ATP by reaction with a phosphate donor, e.g., acetyl phosphate (AcP), catalyzed by a phosphotransferase enzyme, e.g., acetate kinase:

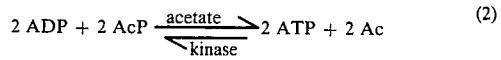  (2)

While this significantly reduced the difficulty in obtaining ATP, it did not eradicate it, largely because commercially acceptable methods of producing the phosphate donors such as acetyl phosphate were not known.

Acetyl phosphate had previously been synthesized from phosphoric acid by acylation with various ingredients, including acetyl chloride, ketene, isopropenyl acetate, and acetic anhydride, followed by isolation as the lithium or silver salts. See Whitesides et al., "Large-Scale Synthesis of Diammonium Acetyl Phosphate," J. Org. Chem., 40:2516 (1975) and refereces cited, incorporated herein by reference. All of these procedures involve difficult work-up and isolation sequences with low yields and/or expensive materials, and none of them are suitable for the preparation of acetyl phosphate in large quantity.

A simpler method for producing acyl phosphate salts, proposed in U.S. Pat. No. 4,088,675, includes acylation of phosphoric acid by a ketene, followed by precipitation of the acyl phosphate as an ammonium salt or a salt of certain organic bases. Further improvements in the process for synthesizing ammonium salts of acyl phosphate were suggested in the commonly assigned U.S. patent application Ser. No. 217,377 (Lewis et al., "Process for Producing Acyl Phosphate Salt," filed Dec. 6, 1980), now abandoned, but the resulting process still involved several steps which require careful experimental control, and which are accordingly difficult to carry out on a large scale. Other disadvantages include the requirement of anhydrous materials, such as 100% phosphoric acid which must be generated from the commercially available 85% phosphoric acid, and the requirement of filtration steps in the procedure. Further, the ammonium ion (used in this preparation to confer crystallinity to the solid product) has two disadvantages. First, it reacts with acetyl phosphate in solution. Second, it forms an insoluble precipitate (magnesium ammonium phosphate) under the reaction conditions. This precipitation both removes from solution the magnesium which may be required for activity of the enzymes [see, e.g., Mildvan, A.S. in *The Enzymes*, 2, 445, ed. Paul D Boyers (1970)], and occludes particles of immobilized enzyme. While the ammonium ion can be exchanged for another cation such as sodium by, for example, treatment with a cation exchange resin, this adds still another manipulation to the procedure, with a corresponding decrease in yield of the product.

There exists a need for a simple, convenient method for the production of acyl phosphate salt in a form that does not interfere with enzymatic reactions.

SUMMARY

This invention consists of the production of a salt of acyl phosphate in an aqueous solution by a process which involves (1) acylation of phosphoric acid ($H_3PO_4$) or its salts ($M_2HPO_4$ or $MH_2PO_4$ where M is a monovalent cation) with an acid anhydride of the general formula RCOX, where R can be hydrogen or a lower alkyl or aryl group having from 1 to 10 carbon atoms, and X can be —OCOR, halogen, —OR, $NR_2$ or any other group which is a good leaving group, followed by (2a) extraction of acyl phosphate to water by treatment of the reaction mixture with an aqueous bicarbonate or hydroxide solution or other basic aqueous solution or (2b) in the case where water has been used as the reaction solvent, acidification with an acid or acid form of a cation exchange resin. After (3) extraction of residual carboxylic acid from the resulting acidic aqueous mixture using a solvent in which the acid is soluble with which water does not mix, the remaining aqueous solution of acyl phosphate is (4) neutralized by addition of a base such as sodium or potassium hydroxide.

If a solution of sodium bicarbonate is used in step (2a) and sodium hydroxide is employed in step (4), the acyl phosphate is generated as its sodium salt, which is frequently preferred, since the sodium ion is generally innocuous as a component of enzyme-containing solutions or suspensions. Substitution of other bases (such as potassium bicarbonate and potassium hydroxide) will result in salts of other cations, which may be preferred if, for example, the sodium ion inhibits the enzyme of interest (e.g., pyruvate kinase).

The reaction scheme may be depicted as follows:

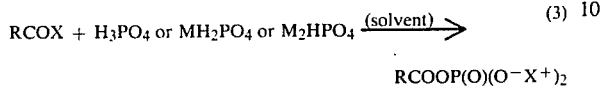

(3)

where M is a monovalent cation. Suitable acylating agents include acetic anhydride, propionic anhydride, butyric anhydride, acetyl chloride, propionyl chloride and the like. Acetic anhydride or acetyl chloride is preferred since they yield acetyl phosphate, which is the preferred substrate for acetate kinase. In addition to the basic bicarbonate and hydroxide solutions described above, other bases such as oxides carbonates, carboxylates, phenoxides or amines may be preferred for particular reactions.

Both 85% and 100% phosphoric acid as well as phosphoric acid salts can be used as starting materials for the reaction. The 85% material is generally more convenient, but requires larger quantities of acylating agent to achieve corresponding yields. While the molar ratio of acylating agent to 85% phosphoric acid may range from about 1:10 to 100:1, the preferred ratio is between 1:2 and 10:1, and the optimal ratio at about 2:1. The preferred range for phosphoric acid salts is 0.5-3.0 M. The preferred pH range for reaction is 5-12. The optimal range is 7-8. Optimal yields are obtained if the pH is maintained in this range throughout the reaction by addition of base (e.g., sodium or potassium hydroxide solutions).

The reaction will proceed using only the acylating agent plus phosphoric acid, but higher yields are obtainable if the reagents are diluted first. Suitable solvents include esters and ketones, with ethyl acetate preferred. Water is the preferred solvent for phosphoric acid salts. The mol ratio of 85% phosphoric acid to solvent may vary widely, from 1:200 to no solvent at all. The preferred range for highest yields is about 1:1 to 1:6.

While the reaction will proceed at temperatures ranging from about $-50°$ C. to $+100°$ C., the preferred range is $-10°$ C. to 50° C. and more preferably between 0° C. and 30° C. As the temperature is increased within this range, the rate of the reaction increases but decomposition of the product becomes more significant, decreasing the ultimate yield of acyl phosphate. When the reagents are relatively concentrated (e.g., 1 mol 85% phosphoric acid: 2 mol acetic anhydride: 1 mol ethyl acetate), the reaction may generate enough heat to raise the temperature above the optimal range; the experimental conditions thus must be carefully regulated to achieve maximal yield. The temperature is less likely to fluctuate with more dilute reagents (e.g., 1 mol phosphoric acid: 2 mol acetic anhydride: 6 mol ethyl acetate), demanding less attention to experimental detail and consistently higher yields, but with longer reaction times.

Most of the carboxylic acid by-product produced during either reaction must be removed before the solution of acyl phosphate can be employed in cofactor regeneration since it may interfere with the enzymes. For example, acetate is a substrate for acetate kinase, and reverses the formation of ATP at high concentrations. The carboxylic acid by-product can be separated from acyl phosphate by any suitable liquid/liquid extraction procedure known to the art; non-limiting examples of suitable solvents are alcohols, esters, ethers and ketones. After extraction, the acyl phosphate product is left in an aqueous solution which is about pH 7, and which can be stored at 0° C. or frozen at $-17°$ C. with less than 5% loss per month. At 24°-27° C., the half-life of acyl phosphate in solution (pH about 7.2) is about 21 hours.

For the problem of acetyl phosphate generation during cofactor regeneration, this invention represents a more practical solution than that reported previously. It has several advantages. First, it can start with commercial 85% phosphoric acid of phosphoric acid salt and does not require conversion of this material to 100% phosphoric acid. Second, it generates the sodium or potassium salt of acyl phosphate directly, and avoids the problems which attend the use of the ammonium salt. Third, the synthesis involves no filtrations; the only manipulations required in purification of the acyl phosphate are liquid-liquid extractions. Fourth, the synthesis involves no experimental steps requiring anhydrous solvents, and should be amenable to scaling up to generate large quantities of acyl phosphate.

DESCRIPTION OF THE PREFERRED EMBODIMENTS

The invention will be further illustrated by the following illustrative embodiments.

EXAMPLE 1

This example illustrates the synthesis of disodium acetyl phosphate in a relatively concentrated solution (1 mol phosphoric acid: 2 mol acetic anhydride: 1 mol ethyl acetate).

Phosphoric acid (85%, 2.0 mol=135 mL) was mixed with ethyl acetate (2 mol=196 mL) in a 1-L flask. The flask was immersed in an ice bath. When the temperature of the solution had reached 13°-15° C. (or lower), acetic anhydride (4 mol=376 mL) was added. The addition rate was regulated to keep the temperature of the reaction mixture between 24°-27° C. All the acetic anhydride was added within 25 min. The solution was left for 5 min at room temperature and then added to a mixture of 1 L of glass distilled water, 500 g of ice and 168 g of sodium bicarbonate in a 5-L flask. The suspension was stirred until no more carbon dioxide was evolved (about 30 min.) The organic layer was separated and discarded. The resulting solution (pH about 3) was extracted at about 4° C. twice with 1.8-L portions and once with a 1.0-L portion of ethyl acetate. After neutralization of the aqueous solution of acetyl phosphate with 10 M sodium hydroxide, about 40 mL of ethyl acetate separated as a second phase. The ethyl acetate layer could be separated using a separation funnel, or removed by decantation if the aqueous solution was frozen for storage. The acetyl phosphate concentration in the final solution (1.7 L) was 1.02 M by enzymatic assay; the yield was 1.73 mol (87%).

The acetate concentration in this preparation of acetyl phosphate was 0.35 M. An alternative extraction procedure can reduce this concentration to less than 0.1M acetate: four extractions using 1.8-L portion of ethyl acetate or two extractions using 3.6-L portions of ethyl acetate, followed by one 1.8-L portion.

EXAMPLE 2

This example illustrates the synthesis of disodium acetyl phosphate in a dilute solution (1 mol phosphoric acid: 2 mol acetic anhydride: 6 mol ethyl acetate). Phosphoric acid (85%, 2.0 mol=135 mL) was dissolved in 1.2 L (12.2 mol) of ethyl acetate in a 2-L flask. The solution was cooled to 0° C., and precooled (0° C.) acetic anhydride (4.0 mol=376 mL) was slowly added over 40 min. The mixture was stirred for 6 h at 0° C. and added to a suspension of ca. 1 L of water, 500 g of ice and 168 g of sodium bicarbonate in a 5-L flask. The resulting mixture was stirred at 0° C. until no more carbon dioxide was evolved. The organic layer was separated and discarded. The resulting solution (pH about 3.0) was washed with one 1.8-L portion and one 1.0-L portion of ethyl acetate to remove most of the acetic acid. After neutrilization of the aqueous solution of acetyl phosphate with 10 M sodium hydroxide, about 40 mL of ethyl acetate separated as a second phase. The ethyl acetate layer was removed as described above. The concentration of acetyl phosphate in the final solution (1.68 L) was 1.10 M by enzymatic assay; the yield was 1.86 mol (93%). The acetate concentration was 0.4 M.

EXAMPLE 3

In this example, disodium acetyl phosphate produced in the manner of Example 2 was used to produce ATP by reaction with ADP in the presence of acetate kinase. The production of ATP was confirmed by conversion of glucose to glucose-6-phosphate by hexokinase using the ATP produced from the disodium acetyl phosphate. A 1-L aqueous solution of glucose (1 mol), ATP (7 mmol), $MgCl_2$ (30 mmol) and 2-mercaptoethanol (17 mmol) was adjusted to pH 7 and deoxygenated. This solution was added to a suspension of immobilized hexokinase (500 U) and acetate kinase (700 U) and left at ambient temperatures under argon. Disodium acetyl phosphate (1.1 mol in 1.2 L of solution) was added over 7 days. The reactor was left for 2 days after the end of acetyl phosphate addition, after which enzymatic assay showed 97% conversion of glucose to glucose-6-phosphate and no significant remaining acetyl phosphate. The solution was separated from the enzyme-containing gel by decantation. A solution of barium chloride (0.25 mol in 200 mL of water) was added, and the precipitated barium phosphate was separated by filtration. An additional quantity of barium chloride (1.3 mol in 700 mL of water) was added, and the barium salt of glucose-6-phosphate was allowed to precipitate for 2 days at 4° C. After filtration and drying, a total of 0.92 mol (92%) of glucose-6-phosphate was obtained (520 g of solid containing 93% barium glucose-6-phosphate as determined by enzymatic assay). The turnover number of ATP during the synthesis was 140, and the activities of enzymes recovered in the gel were hexokinase, 92%; and acetate kinase, 83%.

EXAMPLE 4

This example illustrates the synthesis of disodium propionyl phosphate in a dilute solution. Phosphoric acid (85%, 0.2 mol=13.5 mL) was dissolved in 120 mL of ethyl acetate in a 250-mL flask. The solution was cooled to 0° C., and precooled (0° C.) propionic anhydride (0.8 mol=102 mL) was added over 30 min. The mixture was strired for 4 h at 0° C. and added to a suspension of ca. 100 mL of water, 50 g of ice and 16.0 g of sodium bicarbonate in a 1-L flask. The resulting mixture was stirred at 0° C. until no more carbon dioxide was evolved. The organic layer was separated and discarded. The resulting solution (pH about 3.0 was washed with two 400-mL portions of ethyl acetate to remove most of the propionic acid. After neutralization of the aqueous solution of propionyl phosphate with 10 M sodium hydroxide, about 5 mL of ethyl acetate separated as a second phase. The ethyl acetate layer was removed as described above. The concentration of propionyl phosphate in the final solution (175 mL) was 1.12 M by enzymatic assay; the yield was 0.196 mol (98%). The propionate concentration was 0.3 M.

EXAMPLE 5

In this example, dipotassium acetyl phosphate was produced in manner similar to that of Example 2. Phosphoric acid (85%, 0.2 mol=13.5 mL) was dissolved in 150 mL of ethyl acetate in a 500-mL flask. The solution was cooled to 0° C., and precooled (0° C.) acetic anhydride (0.4 mol=37.6 mL) was slowly added over 3 min. The mixture was stirred for 6h at 0° C. and added to a suspension of ca. 100 mL of water, 100 g of ice and 20.2 g of potassium bicarbonate in a 1-L flask. The resulting mixture was stirred at 0° C. until no more carbon dioxide was evolved. The organic layer was separated and discarded. The resulting solution (pH about 3.0) was washed with two 250-mL portions of ethyl acetate to remove most of the acetic acid. After neutralization of the aqueous solution of acetyl phosphate with 10 M potassium hydroxide, about 5 mL of ethyl acetate separated as a second phase. The ethyl acetate layer was removed as described above. The concentration of acetyl phosphate in the final solution (251 mL) was 0.75 M by enzymatic assay; the yield was 0.19 mol (94%). The acetate concentration was <0.1 M.

EXAMPLE 6

In this example, acetyl phosphate produced in the manner of Example 2 is extracted to water by treatment with a 1 M sodium hydroxide solution. Phosphoric acid (85% 1.6 mol=108 mL) was dissolved in 1.2 L of ethyl acetate in a 2-L flask. The solution was cooled to 0° C., and precooled (0° C.) acetic anhydride (3.0 mol =286 mL) was added over 30 min.

The mixture was stirred for 6 h at 0° C. and slowly added to a suspension of 1 M sodium hydroxide (1.6 L)and 500 g ice in a 3-L flask immersed in a salt water-ice bath. The resulting mixture was at 0° C. for 1 h more after end addition. The solution (pH about 3.0) was washed with 3 2-L portions of ice-cold ethyl acetate to remove most of the acetic acid. After neutralization of the aqueous solution of acetyl phosphate with 10 M sodium hydroxide, about 30 mL of ethyl acetate separated as a second phase. The ethyl acetate layer was removed as described above. The concentration of acetyl phosphate in the final solution (1.56 L) was 0.96 M by enzymatic assay; the yield was 1.50 mol (94%). The acetate concentration was less than 0.1 M.

EXAMPLE 7

In this example, acetyl phosphate produced in the manner of Example 2 is extracted to water by treatment with a 1 M sodium hydroxide pellet-ice-water suspension. Phosphoric acid (85% 1.6 mol=108 mL) was dissolved in 1.2 L of ethyl acetate in a 2-L flask. The solution was cooled to 0° C., and precooled (0° C.)

acetic anhydride (3.0 mol=286 mL) was added over 30 min.

The mixture was stirred for 6 h at 0° C. and slowly added to a suspension of sodium hydroxide pellets (64 g=1.6 mol), 750 mL water and 750 g ice in a 3-L flask immersed in a salt water-ice bath. The resulting mixture was stirred at 0° C. for 1 h after end addition. The solution (pH about 3.0) was washed with 3 2-L portions of ice-cold ethyl acetate to remove most of the acetic acid. After neutralization of the aqueous solution of acetyl phosphate with 10 M sodium hydroxide, about 30 mL of ethyl acetate separated as a second phase. The ethyl acetate layer was removed as described above. The concentration of acetyl phosphate in the final solution (1.53 L) was 0.93 M by enzymatic assay; the yield was 1.42 mol (89%). The acetate concentration was less than 0.1 M.

EXAMPLE 8

This example illustrates the use of acetyl chloride as acetylating agent to produce acetyl phosphate in a manner similar to that of example 2. Phosphoric acid (100%, 0.085 mol=8.35 g) was dissolved in 70 mL of ethyl acetate and cooled to 0° C. Precooled (4° C.) acetyl chloride (0.085 mol, 6.1 mL) was added over 30 min. The mixture was stirred for 1 h at 0° C. and added to a suspension of ca. 50 mL of water, 30 g of ice and 7.1 g of sodium bicarbonate in a 250-mL flask. The resulting mixture was stirred at 0° C. until no more carbon dioxide was evolved. The organic layer was separated and discarded. The resulting solution (pH about 3.0) was washed with two 200-mL portions of ethyl acetate to remove most of the acetic acid. After neutralization of the aqueous solution, the acetyl phosphate concentration (68 mL) was 0.35 M by enzymatic assay; the yield was 0.024 mol (28%).

EXAMPLE 9

This example illustrates the use of acetyl chloride to aceylate the monolithium salt of phosphoric acid in ethyl acetate. Phosphoric acid (100%, 4.4 g-0.045 mol) dissolved in ethyl acetate (50 mL) was added to Lithium carbonate (1.7 g-0.0224 mol) with vigorous stirring. When no more carbon dioxide was evolved the suspension was cooled to 0° C. and precooled acetyl chloride (4.0 mL-0.056 mol) was added over the course of 15 min. The suspension was stirred at 0° C. for 8 hours, the solid was removed by filtration and the filtrate was added to a suspension of 10 g of ice, 4.7 g of sodium bicarbonate and 40 mL of water. After stirring the suspension for 1 h, the organic layer was separated and discarded. The resulting solution (pH approximately 3.0) was washed with two 100-mL portions of ethyl acetate to remove most of the acetic acid. After neutralization of the aqueous solution (46 mL) the acetyl phosphate concentration was 0.70 M by enzymatic assay; the yield was 0.032 mol (72%).

EXAMPLE 10

This example illustrates the synthesis of dipotassium acetyl phosphate starting with aqueous $K_2HPO_4$ and acetic anhydride. After reaction the reaction mixture is acidified with the acid form of exchange resin and the acetic acid removed using liquid-liquid extraction with ethyl acetate. Dipotassium hydrogen phosphate ($K_2HPO_4$, 1.0 L of 2.0 M solution) in a 4-L Ehrlenmeyer flask was adjusted to pH 7.8 with concentrated HCl and cooled to 0°±2° C. in an ice-salt water bath. Acetic anhydride (0.38 L) was added over 4 h to the stirred reaction mixture. The pH was maintained at 7.8+0.5 using a pH controller which regulated the addition of 10 N KOH; 0.60 L was required. The reaction was complete after 5.5 h as evidenced by no further change in pH and by the disappearance of all the acetic anhydride which floated on the solution as a separate phase during reaction. Enzymatic assay showed 0.93 M acetyl phosphate (~2 L of solution; ~93% yield based on phosphate). The solution was acidified to pH 3.0 by addition of 3.6 kg (~8 moles acid) of the hydrogen form of the cation exchange resin Dowex 50W-X8 (Dow Chemical Co.; a cross-linked polystyrene functionalized with sulfonate groups). The resin was separated by decantation and washed with 0.20 L of water. The solution was extracted four times with 4.0 L of cold (0° C.) ethyl acetate, then neutralized with 10 N KOH to pH 7.0 and stored at −12° C. Enzymatic assay showed 0.98 M acetyl phosphate (2.1 L; 1.9 moles; 94% yield based on phosphate). $^1H$ NMR spectroscopy showed that the solution also contained 0.12 M acetate and 0.50 M ethyl acetate.

EXAMPLE 11

This example illustrates the synthesis of acetyl phosphate as a mixed sodium-potassium salt starting with aqueous $K_2HPO_4$ and acetic anhydride. In this example after reaction the reaction mixture is acidified with HCl and the acetic acid removed using liquid-liquid extraction with ethyl acetate. Dipotassium hydrogen phosphate ($K_2HPO_4$, 0.50 L of 2.0 M solution) was adjusted to pH 7.8 with 0.015 L of 12 N HCl and cooled to 0° C. in an ice-salt water bath. Acetic anhydride (0.19 L) was added over 2 h while stirring the reaction mixture with a magnetic stirrer. The pH was maintained at 7.9±0.5 using a pH controller which regulated the addition of 10 N NaOH; 0.32 L was required. The reaction was judged complete after four hours as evidenced by no further change in pH and by the disappearance of all the acetic anhydride which floated on the solution as a separate phase during reaction. Enzymatic assay showed 0.90 M acetyl phosphate (~92% yield based on phosphate).

The solution was acidified to pH 3.0 by adding 0.30 L of 12 N HCl (total volume ~1.4 L) and extracted four times with 2.8-L portions of cold (0° C.) ethyl acetate. The solution was neutralized to pH 7.8 with 0.05 L of 10 N NaOH and stored at −12° C. Enzymatic assay showed 0.79 M acetyl phosphate (1.1 L; 87% yield based on phosphate). $^1H$ NMR spectroscopy showed that the solution contained <0.01 M acetate. Based on the reagents added throughout preparation, the MCl (M=Na, K) concentration is estimated as 5.5 M.

EXAMPLE 12

This example illustrates the preparation of dipotassium propionyl phosphate starting the aqueous $KH_2PO_4$ and propionic anhydride. After reaction the reaction mixture is acidified with the acid form of a cation exchange resin and the propionic acid removed using liquid-liquid extraction with ethyl acetate.

Dipotassium hydrogen phosphate (100 mL of aqueous 1.0 M solution) was adjusted to pH 7.8 with several mL of 50 wt % KOH solution. The phosphate solution was cooled to 0° C. in an ice-water bath. Propionic anhydride (26 mL, 0.20 mol) was added in several portions over 3 h. The pH of the solution was monitored continuously with a pH electrode and was maintained at 7.2-8.3 by manual addition of 50 wt % KOH solution. A total of ~40 mL was required. After 13 h the reaction was judged complete since pH changes no longer occurred; in addition, no more propionic anhydride could be observed as a second phase.

Dowex 50W-X8 (polystyrene beads containing sulfonic acid functionalities; acid form, ~200 g) were used to bring the pH of the solution to 3.0. The Dowex resin was removed by filtration and washed with 20 mL of $H_2O$. The combination of filtrate and wash (~200 mL) was extracted three times with 400-mL portions of cold (0° C.) ethyl acetate. The aqueous phase was adjusted to pH 7.0 with 50 wt % KOH and stored at −12° C. It is important to keep solutions cold (0° C.) during manipulations to minimize hydrolysis. Phosphorous NMR spectroscopy of the final solution showed 78% of the phosphorous as propionyl phosphate ($-1.7\delta$), the remainder as inorganic phosphate ($2.2\delta$) corresponding to a 78% yield based on phosphorous, 38% based on propionic anhydride.

We claim:

1. A method of preparing a monoacyl phosphate salt chosen from the group of sodium and potassium salts and mixtures thereof, comprising the steps of (a) reacting a phosphorus-containing compound selected from the group of phosphoric acid and phosphoric acid salts having the formula $MH_2PO_4$ or $M_2HPO_4$, where M is sodium or potassium, with an acylating agent selected from the group consisting of lower acyl anhydrides and halides in a organic solvent selected from the group consisting of esters and ketones, the molar ratio of phosphorous-containing compound to said organic solvent being between about 1:1 and 1:10 and the ratio of said acylating agent to said phosphorus-containing compound being between about 1:2 and 10:1, the reaction temperature being maintained between about 0° C. and 30° C.; (b) treating the resulting product with a basic sodium or potassium aqueous solution in an amount effective to maintain the pH between about 5 and 12 and to extract the acyl phosphate to water; (c) separating the acyl phosphate salt from the reaction mixture as an aqueous solution; and (d) extracting residual carboxylic acids from the aqueous solution of acyl phosphate.

2. The method of claim 1 wherein the acylating agent is acetic anhydride.

3. The method of claim 1 wherein the acylating agent is propionic anhydride.

4. The method of claim 1 wherein the acylating agent is acetyl chloride.

5. The method of claim 1 wherein the carboxylic acids are removed by liquid-liquid extraction.

6. The method of claim 5 wherein the extraction step is conducted using a solvent selected from the group of esters, ethers, alcohols and ketones.

7. The method of claim 6 wherein the post-extraction solution of acyl phosphate is then neutralized and frozen for storage.

8. A method of preparing a monoacyl phosphate salt chosen from the group of sodium and potassium salts and mixtures thereof, comprising the steps of (a) reacting an aqueous solution of a phosphorous-containing compound selected from the group of phosphoric acid and phosphoric acid salts having the formula $MH_2PO_4$ or $M_2HPO_4$, where M is sodium or potassium, with an acylating agent selected from the group consisting of lower acyl anhydrides and halides, the ratio of said acylating agent to said phosphorus-containing compound being between about 1:2 and 10:1, the reaction temperature being maintained between about 0° C. and 30° C. and the reaction pH being maintained between about 5 and 12; (b) acidifying the reaction mixture to a pH of about 3 to protonate carboxylic by-products; and (c) extracting residual carboxylic acids from the aqueous solution of acyl phosphate.

9. The method of claim 8 wherein the step of acidifying the reaction mixture further comprises employing an acid form of a cationic exchange resin to lower to pH to about 3.

10. The method of claim 8 wherein the step of acidifying the reaction mixture further comprises treating the mixture with an acid in an amount effective to lower the pH to about 3.

11. The method of claim 8 wherein the carboxylic acids are removed by liquid-liquid extraction.

12. The method of claim 11 wherein the extraction step is conducted using a solvent selected from the group of esters, ethers, alcohols and ketones.

13. The method of claim 12 wherein the post-extraction solution of acyl phosphate is then neutralized and frozen for storage.

* * * * *